United States Patent [19]

Maurer et al.

[11] Patent Number: 5,385,577
[45] Date of Patent: Jan. 31, 1995

[54] ELECTRODE FOR ACTIVATING PELVIC REFLEXES

[75] Inventors: Donald D. Maurer, Marine on the St. Croix; Mary M. Lien, Arden Hills, both of Minn.

[73] Assignee: Empi, Inc., St. Paul, Minn.

[21] Appl. No.: 975,518

[22] Filed: Nov. 12, 1992

[51] Int. Cl.⁶ .................... A61N 1/05; A61N 1/36
[52] U.S. Cl. ........................ 607/41; 607/138
[58] Field of Search ............ 128/788, 801, 802, 419 S, 128/401; 607/39–41, 66, 138

[56] References Cited

U.S. PATENT DOCUMENTS

| | | | |
|---|---|---|---|
| 1,253,955 | 1/1918 | Galligan . | |
| 1,704,000 | 3/1929 | Herwig et al. . | |
| 2,085,644 | 6/1937 | Ferciot | 128/407 |
| 2,126,257 | 8/1938 | Hird | 128/303.11 |
| 3,403,684 | 10/1968 | Stiebel et al. | 128/788 |
| 3,749,100 | 7/1973 | Von Der Mosel | 128/407 |
| 3,800,800 | 4/1974 | Garbe et al. | 128/408 |
| 3,933,147 | 1/1976 | Du Vall et al. | 128/2 S |
| 4,094,309 | 6/1978 | Grzenia | 128/2.06 |
| 4,124,028 | 11/1978 | Gallo | 128/419 S X |
| 4,296,760 | 10/1981 | Carlsson et al. | 128/788 |
| 4,406,288 | 9/1983 | Horwinski et al. | 128/422 |
| 4,564,024 | 1/1986 | Wohler, Jr. | 128/419 S X |
| 4,688,575 | 8/1987 | DuVall | 128/422 |
| 4,785,828 | 11/1988 | Maurer | 128/788 |
| 4,873,996 | 10/1989 | Maurer | 128/844 |
| 4,881,526 | 11/1989 | Johnson et al. | 128/24.5 |
| 4,909,263 | 3/1990 | Norris | 128/788 |
| 5,117,840 | 6/1992 | Brenman et al. | 128/788 |
| 5,199,443 | 4/1993 | Maurer et al. | 128/788 |
| 5,213,097 | 5/1993 | Zeindler | 128/401 |
| 5,233,987 | 8/1993 | Fabian et al. | 607/41 |

FOREIGN PATENT DOCUMENTS

| | | |
|---|---|---|
| 2387049 | 4/1978 | France . |
| 2547203 | 6/1983 | France . |
| 2622458 | 5/1989 | France . |
| 2822616 | 11/1979 | Germany . |
| 8807819.1 | 9/1988 | Germany . |
| 8807820.5 | 9/1988 | Germany . |
| WO84/01515 | 4/1984 | WIPO . |

OTHER PUBLICATIONS

Empi, Inc., *Innova Feminite Incontinence Treatment System Design Rationale*, 1992.
Empi, Inc., *Innova*, 1991, 1992.
*Intravaginal Stimulation for Urinary Incontinence Selected Abstracts*.
Ivan A. Brezovich, Ph. D.; Michael B. Lilly, M.D.; John R. Durant, M.D.; and Diane B. Richards, R.N.; *A Practical System for Clinical Radiofrequency Hyperthermia*, Mar. 1981, vol. 7, pp. 423–430.
*Electrical Treatment of Anal Incontinence* by B. R. Hopkinson, R. Lightwood, "The Lancet", pp. 297–298, Feb. 5, 1966.
*Guard for Intra-Anal Plug Electrode*, by E. S. Glen, "The Lancet", pp. 325–326, Aug. 9, 1969.

*Primary Examiner*—Lee S. Cohen
*Attorney, Agent, or Firm*—Kinney & Lange

[57] ABSTRACT

An electrode for activating pelvic reflexes in a patient is made of a molded elongated tubular member and a patient conforming handle member. The tubular member has a plurality of conductive polymer bands separated by at least one nonconductive polymer band. The patient conforming handle member connects to the distal end of the tubular member for properly positioning the electrode and for preventing movement of the electrode in either a proximal or a distal direction.

35 Claims, 2 Drawing Sheets

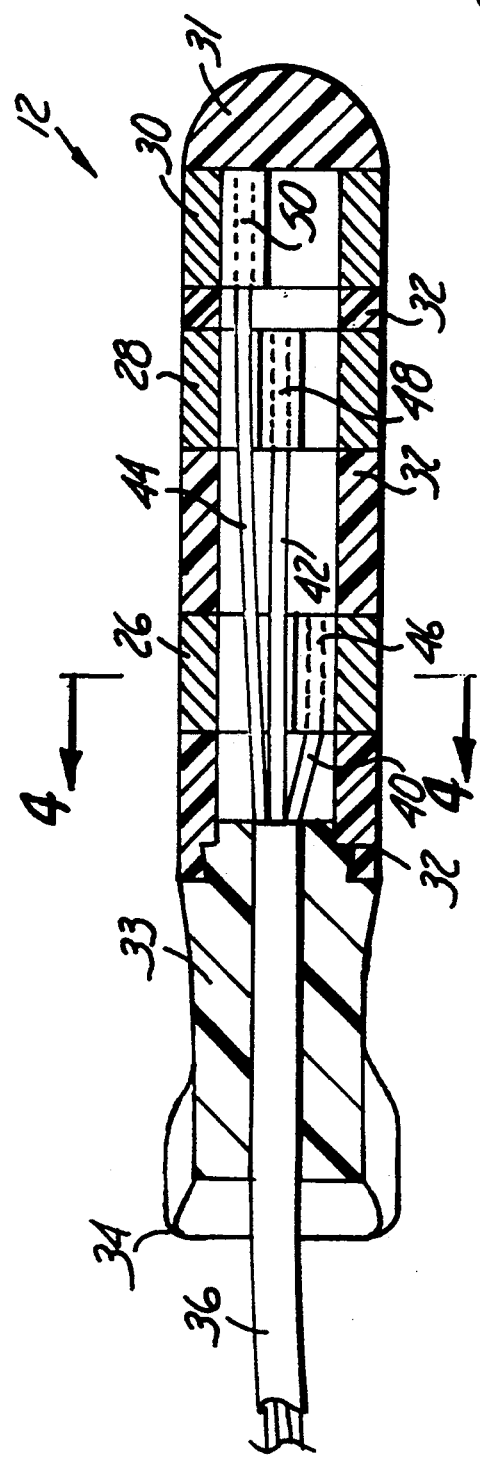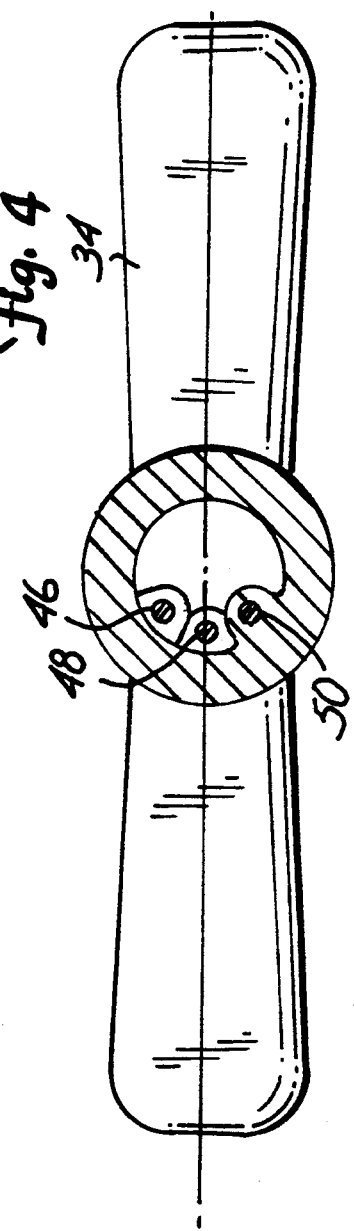

ELECTRODE FOR ACTIVATING PELVIC REFLEXES

BACKGROUND OF THE INVENTION

The present invention relates generally to the field of electrical neuromuscular stimulation for treatment of incontinence. In particular, the present invention is a molded electrode device with handle having increased efficacy, safety, and comfort.

Incontinence affects an estimated 12–15 million adults nationwide. Defined as the inability to retain urine or feces through loss of sphincter control, incontinence costs society an estimated $10.3 billion annually.

Electrical neuromuscular stimulation is widely used to assist persons afflicted with motor or nerve dysfunctions in performing muscle contraction maneuvers. This technique is also used to re-educate patients in the proper use of the dysfunctional muscles. For the treatment of incontinence, pulses of electrical current stimulate sensory nerve fibers located within the vagina or rectum. This in turn causes reflex contractions of the pelvic floor muscles and reflex inhibition of a spastic bladder muscle.

"Stress incontinence" can result from the patient's inability to properly contract or close the external sphincter of the urethra when there is increased pressure on the bladder, such as during coughing or lifting. It has been shown that neuromuscular stimulation can cause contractions of the pelvic floor by means of a vaginal or anal electrode which effectively prevents the unwanted leakage of urine. Furthermore, through the use of such an electrode, patients can educate themselves to voluntarily or automatically impede the flow of urine. Another important application of the pelvic floor contractions is the exercise and toning of the muscles of the pelvic floor which support the bladder, urethra, and other organs. Pelvic floor muscles which have become lax or stretched due to either the process of child birth, obesity, multiple sclerosis, or degenerative changes associated with aging can be strengthened and tightened to properly support the particular organs, thus positively affecting the patient's ability to maintain continence.

Another common form of incontinence is called "urge incontinence". This condition results from a hyperactive or spastic bladder muscle. Electrical stimulation to sensory nerve fibers can activate certain reflex contractions of the pelvic floor muscles which inhibit the inappropriate bladder contractions associated with urge incontinence.

Anal incontinence is a similar problem. It is the inability to prevent the involuntary expulsion of gas, liquid, or solids from the lower bowel. The ani sphincter muscles of continent persons prevent involuntary expulsions from the lower bowel. The ani sphincter is made up of two distinct muscles; the external anal sphincter and the internal anal sphincter. The external sphincter, made up of striated muscles, is capable of voluntary control. Conversely, the internal sphincter, made up of smooth muscle, is incapable of voluntary control. Once again, neuromuscular stimulation via an anal electrode can cause contractions of pelvic floor muscles, including the dysfunctional external sphincter muscle to effectively prevent incontinence. Furthermore, patients can educate themselves to voluntarily or automatically prevent these involuntary expulsions.

Electrical neuromuscular stimulation has become a recognized and accepted form for the treatment of incontinence. Several prior art references disclose vaginal or anal electrodes for the prevention of incontinence. However, these prior art references have short-comings which limit their effectiveness. First, prior art electrodes have a tendency to be pulled inward into the rectum during stimulation periods due to muscle contractions of pelvic floor muscles. They also have a tendency to fall out of the vagina or rectum during non-stimulation periods. Second, the diameter and rigid composition of prior art electrodes often cause discomfort and pain to the patient.

Therefore, there is a continuing need for an improved flexible electrode for use in the vagina or rectum which can effectively restore continence, is securely held in place during either stimulation or non-stimulation periods, and will be comfortable to the patient.

SUMMARY OF THE INVENTION

The present invention provides an electrode device having increased efficacy, safety, and comfort. The electrode has a handle at its distal end to prevent the electrode from being pulled inward into the rectum during stimulation periods and from falling out of the rectum during non-stimulation periods. Also, both the length and diameter of the electrode have been reduced for the comfort and safety of the patient.

The electrode, which controls incontinence in a patient by activating pelvic floor muscles, incorporates a molded elongated tubular member having a plurality of conductive polymer bands separated by at least one nonconductive polymer band. A flexible and anatomically correct handle member connected to the distal end of the tubular member properly positions the electrode within the rectum and prevents movement of the electrode in either a proximal or a distal direction. The handle member fits comfortably between the gluteal muscles of the patient.

BRIEF DESCRIPTION OF THE DRAWINGS

FIG. 3 is a longitudinal sectional view of the present invention.

FIG. 4 is sectional end view of the present invention as viewed from a line 4—4 of FIG. 3.

DETAILED DESCRIPTION OF THE PREFERRED EMBODIMENTS

Figure 1:
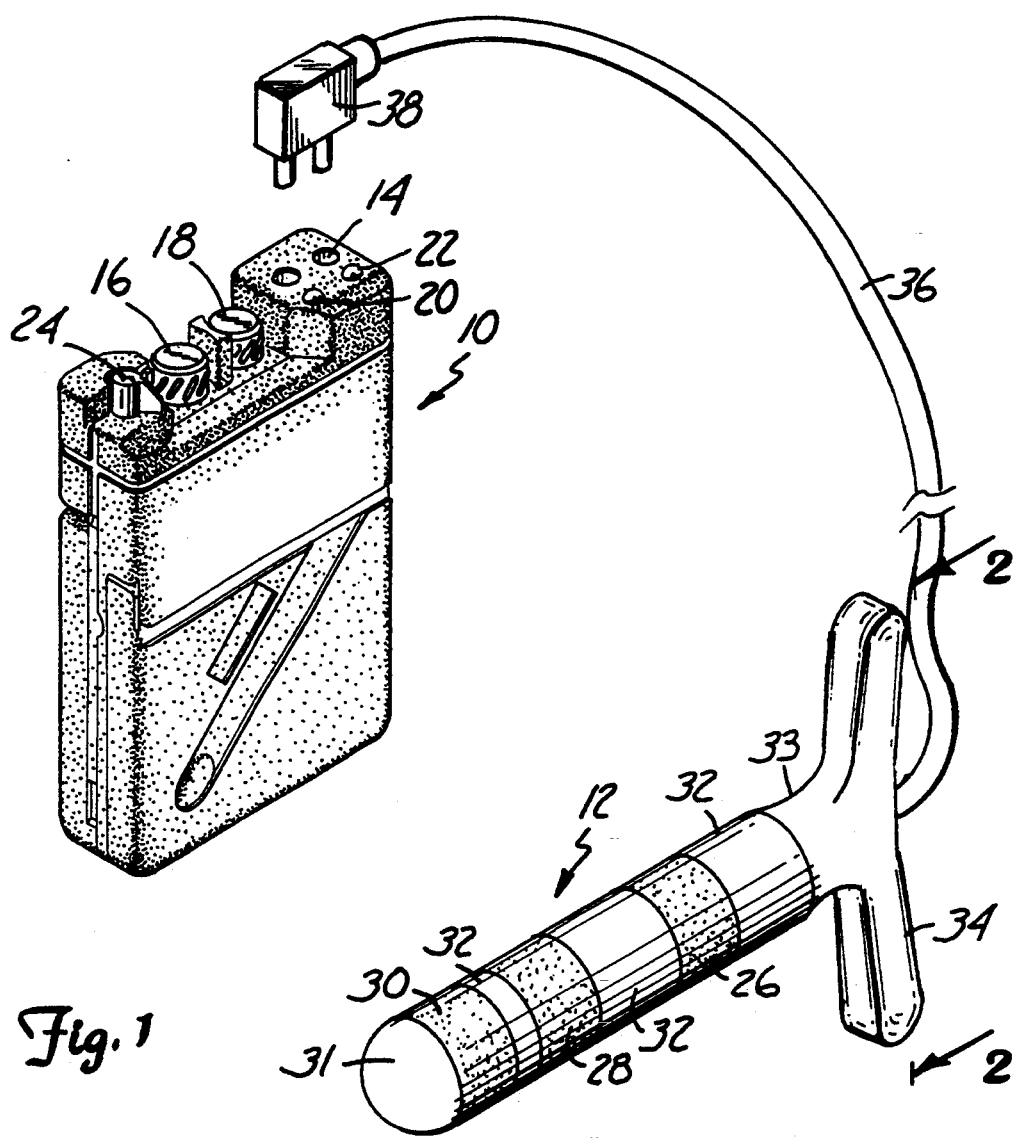
FIG. 1 is a perspective view of the present invention.

A portable patient treatment device 10 and treatment electrode 12 are shown in FIG. 1. Portable patient treatment device 10 includes port 14, first channel control 16, second channel control 18, operation lights 20 and 22, and timed treatment control 24. Treatment electrode 12 includes first conductive polymer electrode 26, second conductive polymer electrode 28, third conductive polymer electrode 30, tip 31, non-conductive polymer bands 32, neck 33, handle 34, cable 36, and plug 38.

During operation, treatment electrode 12 is connected to portable patient treatment device 10 by cable 36. For patient stimulation, treatment electrode 12 is inserted into a patient's rectum while plug 38 is connected into portable patient treatment device 10 via port 14.

Treatment electrode 12 is a two channel device. First conductive polymer electrode 26 and second conductive polymer electrode 28 form a first electrode pair while first conductive polymer electrode 26 and third conductive polymer electrode 30 form a second electrode pair. First conductive polymer electrode 26, therefore, is common to both electrode pairs. First electrode pair provides stimulation to the patient at a first frequency while second electrode pair provides stimulation at a second frequency, wherein the first frequency is a different frequency than the second frequency. First and second channel controls 16 and 18 control the electrical pulse stimulation signals supplied to first conductive polymer electrode pair (electrodes 26 and 28) and second conductive polymer electrode pair (electrodes 26 and 30) respectively. The first and second frequencies may be phased so that the electrical pulse stimulation signals controlled by first and second channel controls 16 and 18 do not overlap.

Operation light 20 indicates when the first channel is in operation while operation light 22 indicates when the second channel is in operation. Time treatment control 24 provides the option of running the patient stimulation for various intervals with automatic shut-off.

Handle 34 and neck 33 properly position treatment electrode 12 within the patient's rectum and prevents movement of treatment electrode 12 in either a proximal or a distal direction. In a preferred embodiment, the angle between each wing of handle 34 and neck 33 is in the range of approximately 90° to 110° and the angle between the two wings of handle 34 is in the range of approximately 180° to 220°. These dimensions allow handle 34 to fit comfortably between the patient's gluteal muscles while the patient's external ani sphincter muscle encompasses neck 33.

Figure 2:
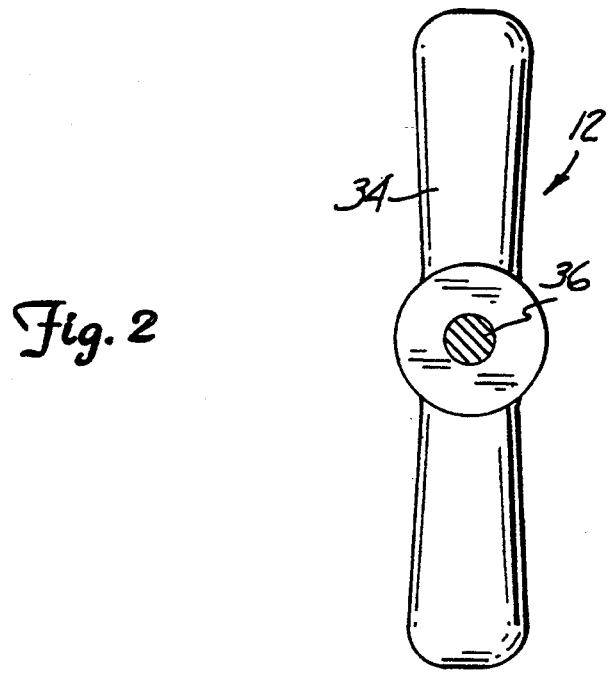
FIG. 2 is an end view of the present invention as viewed from a line 2—2 of FIG. 1.

FIG. 2 is an end view of the present invention as viewed from a line 2—2 of FIG. 1. As can be seen from FIG. 2, cable 36 is positioned through the center of handle 34. Also, in a preferred embodiment, the width of each wing of handle 34 increases as the distance from cable 36 increases. In a preferred embodiment, the width of each wing of handle 34 ranges from approximately 0.450 inches near the center of handle 34 to approximately 0.555 inches away from the center of handle 34. Similarly, in a preferred embodiment, the length of handle 34 is approximately 3.100 inches. These dimensions provide for maximum patient comfort.

FIG. 3 is a longitudinal sectional view of the present invention. Treatment electrode 12 includes first conductive polymer electrode 26, second conductive polymer electrode 28, third conductive polymer electrode 30, tip 31, non-conductive polymer bands 32, neck 33, handle 34, cable 36, first wire 40, second wire 42, third wire 44, first electrical lead 46, second electrical lead 48, and third electrical lead 50.

First wire 40 provides electrical current to first conductive polymer electrode 26 through first electrical lead 46, while second wire 42 and third wire 44 provide energizing current to second conductive polymer electrode 28 and third conductive polymer electrode 30 through second electrical lead 48 and third electrical lead 50, respectively.

Treatment electrode 12 is made of a tubular polymeric construction which ensures radial flexibility. This radial flexibility of treatment electrode 12 permits the patient's rectal musculature to contract against treatment electrode 12 with a minimum compression of pressure sensors in the rectal tissue. This results in improved comfort for the patient. Patients using prior art electrodes often suffer from capillary compression, which is common when the pelvic floor muscles contract around a rigid electrode, resulting in both reduced blood flow to the muscles and an anaerobic contraction. The radial flexibility of treatment electrode 12 helps avoid muscle fatigue caused by an anaerobic contraction by substantially preventing capillary compression when the pelvic floor muscles contract around treatment electrode 12.

In a preferred embodiment, the durometer of treatment electrode 12 is between 30 to 90 shore A, with a durometer of 30 to 60 shore A being most preferable. In addition, for patient comfort, the wall thickness of treatment electrode 12 is between about 0.0625 to 0.250 inches, with a thickness of 0.125 to 0.250 inches being most preferable. Electrode 12 preferably has an outer diameter of about 0.550 to 1.100 inches and an inner diameter of about 0.400 to 0.600 inches.

Conductive polymer electrodes 26, 28, and 30, have a volume resistivity of between about 1 to 500 ohm-centimeters, which closely approximates the impedance of a human's rectal tissue. More preferably, the volume resistivity is in the range of about 1 to 100 ohm-centimeters. This close impedance match between a human's rectal tissue and conductive polymer electrodes 26, 28, and 30 substantially eliminates "edge effect" current density burns to the rectal tissue. In a preferred embodiment, volume resistivity of conductive polymer electrodes 26, 28, and 30 ranges from about 5 to 20 ohm-centimeters, thus providing the most comfortable therapy session for a patient.

For maximum patient comfort, conductive polymer electrodes 26, 28, and 30 and non-conductive polymer bands 32 have an outer diameter of approximately 0.700 inches, an interior diameter of approximately 0.425 inches, and a wall thickness of about 0.140 inches. Likewise, for maximum patient comfort, the distance from tip 31 to neck 33 is about 2.000 to 3.500 inches (and preferably about 2.750 inches). Also, the spacing between first electrode 26 and second electrode 28 is approximately 0.350 to 0.750 inches, and the spacing between second electrode 28 and third electrode 30 is approximately 0.075 to 0.250 inches. This spacing allows second conductive polymer electrode 28 and third conductive polymer electrode 30 to be properly positioned within the rectum so that maximum stimulation is provided to the motor nerve fibers located within the rectum. This in turn causes reflex contractions of the pelvic floor muscles, including the innervated muscles causing incontinence. Therefore patients can re-educate themselves on the proper use of the dysfunctional muscles.

FIG. 4 is a sectional end view of the present invention as viewed from a line 4—4 of FIG. 3. FIG. 4 shows the proper position of electrical leads 46, 48, and 50. Electrical leads 46, 48, and 50 should be clustered near one wing of handle 34 for maximum patient comfort. Improper location of electrical leads 46, 48, and 50 can result in pain and discomfort to the patient.

Treatment electrode 12 provides a patient with an improved flexible electrode for the prevention of incontinence which can be held securely in the proper position during either stimulation or non-stimulation periods, and will be comfortable to the patient.

Although the present invention has been described with reference to preferred embodiments, workers skilled in the art will recognize that changes may be made in form and detail without departing from the spirit and scope of the invention.

What is claimed is:

1. An electrode for controlling incontinence in a patient, the electrode comprising:
   a molded elongated tubular member having a proximal end, a distal end, a longitudinal axis, first, second, and third conductive polymer bands, a first nonconductive polymer band positioned between the first and second conductive polymer bands, and a second nonconductive polymer band positioned between the second and third conductive polymer bands;
   a patient conforming handle member connected to the distal end of the tubular member for properly positioning the electrode and for preventing movement of the electrode in either a proximal or a distal direction; and
   wherein the first and second conductive polymer bands form a first electrical circuit and provide electrical stimulation at a first frequency and the first and third conductive polymer bands form a second electrical circuit and provide electrical stimulation at a second frequency, wherein the second frequency is different from the first frequency.

2. The electrode of claim 1 wherein the tubular member has an exterior diameter in the range of about 0.550 to 1.100 inches.

3. The electrode of claim 1 wherein the tubular member has a length in the range of about 2.000 to 3.500 inches.

4. The electrode of claim 1 wherein the patient conforming handle member comprises:
   a body; and
   a first wing.

5. The electrode of claim 4 wherein the angle between the first wing and the body is in the range of about 90 to 110 degrees.

6. The electrode of claim 4 wherein the patient conforming handle member further comprises:
   a second wing.

7. The electrode of claim 6 wherein the angle between the second wing and the body is in the range of about 90 to 110 degrees.

8. The electrode of claim 6 wherein the angle between the first wing and the second wing is in the range of about 180 to 220 degrees.

9. The electrode of claim 1 wherein each conductive polymer band has a width and electrical coupling means at an interior surface of each conductive polymer band.

10. The electrode of claim 1 wherein the tubular member comprises:
    an interior cavity;
    an interior surface; and
    an exterior surface.

11. The electrode of claim 10 wherein the interior cavity has a diameter in the range of about 0.400 to 0.450 inches.

12. The electrode of claim 10 wherein the tubular member has a wall thickness in the range of about 0.0625 to 0.250 inches.

13. The electrode of claim 10 wherein the conductive and nonconductive polymer bands have a durometer measurement in the range of about 30 to 90 shore A.

14. The electrode of claim 10 wherein the conductive and nonconductive polymer bands have a durometer measurement in the range of about 30 to 60 shore A.

15. The electrode of claim 1 wherein the conductive polymer bands have a volume resistivity in a range of about 1 to 500 ohm-centimeters.

16. The electrode of claim 1 wherein the conductive polymer bands have a volume resistivity in a range of about 1 to 100 ohm-centimeters.

17. The electrode of claim 1 wherein the conductive polymer bands have a volume resistivity in a range of about 5 to 20 ohm-centimeters.

18. The electrode of claim 1 wherein the first conductive polymer band is separated from the second conductive polymer band by a distance in the range of about 0.350 to 0.750 inches.

19. The electrode of claim 1 wherein the second conductive polymer band is separated from the third conductive polymer band by a distance in the range of about 0.075 to 0.250 inches.

20. An electrode for activating pelvic reflexes in a patient, the electrode comprising:
    a molded elongated tubular member having a proximal end, a distal end, a longitudinal axis, first, second, and third conductive polymer bands, a first nonconductive polymer band positioned between the first and second conductive polymer bands, and a second nonconductive polymer band positioned between the second and third conductive polymer bands;
    a patient conforming handle connected to the distal end of the tubular member, wherein the handle comprises:
    a body;
    a first arm connected to the body at a first angle of about 90 to 110 degrees; and
    a second arm connected to the body at a second angle of about 90 to 110 degrees; and
    wherein the first and second conductive polymer bands form a first electrical circuit and provide electrical stimulation at a first frequency and the first and third conductive polymer bands form a second electrical circuit and provide electrical stimulation at a second frequency, wherein the second frequency is different from the first frequency.

21. An electrode for controlling incontinence in a patient, the electrode comprising: a molded elongated tubular member comprising:
    a first conductive polymer band for providing electrical stimulation at a first frequency;
    a second conductive polymer band for providing electrical stimulation at a second frequency;
    a third conductive polymer band wherein the first and third conductive polymer bands form a first electrical circuit and provide electrical stimulation at the first frequency and the second and third conductive polymer bands form a second electrical circuit and provide electrical stimulation at the second frequency; and
    wherein the second frequency is different from the first frequency; and a plurality of leads connected to respective first, second and third conductive polymer bands for providing energizing current to the first, second, and third conductive polymer bands.

22. The electrode of claim 21 and further comprising: a patient conforming handle member connected to a distal end of the tubular member for properly positioning the electrode within a body cavity and for preventing movement of the electrode in either a proximal or a distal direction.

23. A system for controlling incontinence in a patient, the system comprising:

an electrode having an elongated tubular body, the elongated tubular body having an interior surface and an exterior surface, the tubular body further having first, second and third conductive regions, each conductive region separated by at least one non-conductive region, the first, second and third conductive regions configured to provide a first current path and a second current path, wherein the first and second current paths share one of the conductive regions; and electrical stimulation means communicating with the first, second and third conductive regions, for delivering a first signal at a first frequency to the first current path, and for delivering a second signal at a second frequency, different from the first frequency, to the second current path.

24. The system of claim 23 wherein the first current path comprises:

the first conductive region and the second conductive region, and the first and second conductive regions are positioned at opposite ends of the tubular body.

25. The system of claim 24 wherein the second current path comprises:

the first conductive region and the third conductive region, and the third conductive region is positioned between the first conductive region and second conductive region.

26. The system of claim 25 wherein the tubular body has a length of about 2.00 to about 3.50 inches.

27. The system of claim 23 wherein the elongated tubular body has a durometer of between about 30 to about 90 shore A.

28. The system of claim 27 wherein the elongated tubular body has a durometer of between about 30 to about 60 shore A.

29. A dual channel stimulating system for controlling incontinence comprises:

an elongated tubular body, having first, second and third conductive regions longitudinally spaced along the tubular body, each conductive region separated from an adjacent conductive region by at least one non-conductive region; and electrical stimulation means communicating with the first, second and third conductive regions for delivering a first signal at a first frequency to the first and third conductive regions, and for delivering a second signal at a second frequency, to the first and second conductive regions, wherein the second frequency is different from the first frequency.

30. The stimulation system of claim 29 wherein the first conductive region and the third conductive region are positioned at opposite ends of the tubular body.

31. The stimulation system of claim 30 wherein the second conductive region is positioned between the first conductive region and the third conductive region.

32. The stimulation system of claim 31 wherein the tubular body has a length of about 2.00 to about 3.50 inches.

33. The stimulation system of claim 29 wherein the elongated tubular body has a durometer of about 30 to about 90 shore A.

34. The stimulation system of claim 29 wherein the elongated tubular body has a durometer of about 30 to about 60 shore A.

35. A method of treating incontinence, the method comprising:

inserting into a body cavity an electrode comprising a tubular body having first, second and third conductive regions separated by at least one non-conductive region;

applying a first signal having a first frequency to a first electrode pair formed by the first and third conductive regions to provide electrical stimulation to tissue at the first frequency;

applying a second signal having a second frequency to a second electrode pair formed by the first and second conductive regions to provide electrical stimulation to tissue at the second frequency; and wherein the second frequency is different from the first frequency.

* * * * *